Figure 1:
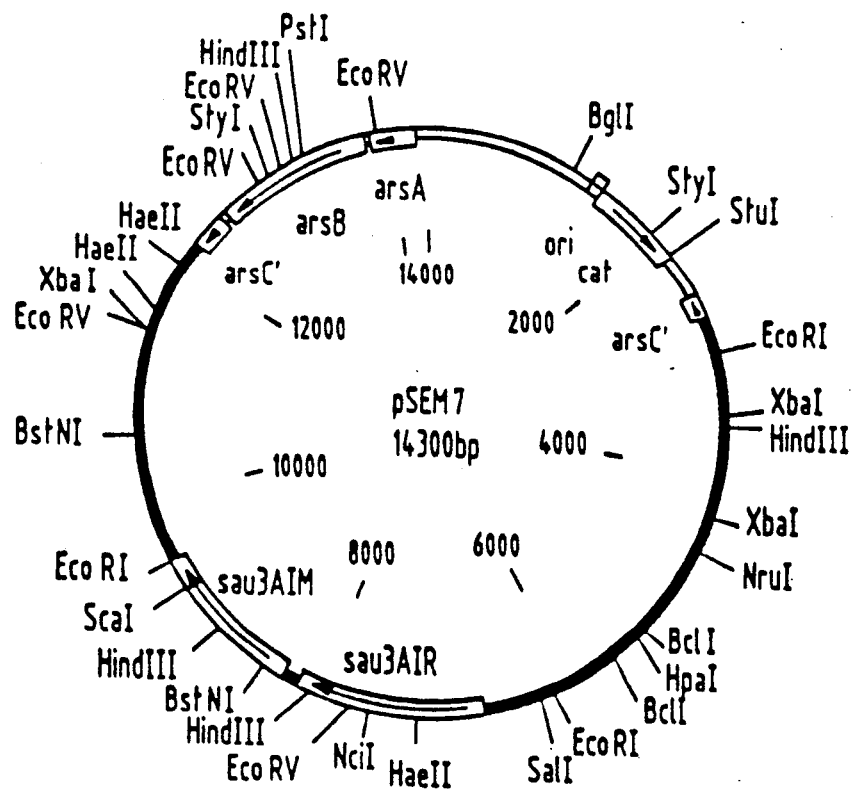

United States Patent [19]

Götz et al.

[11] Patent Number: 5,175,101

[45] Date of Patent: Dec. 29, 1992

[54] RECOMBINANT RESTRICTION ENZYME SAU3AI

[75] Inventors: Friedrich Götz, Tübingen; Stefan Seeber, Munich, both of Fed. Rep. of Germany

[73] Assignee: Boehringer Mannheim GmbH, Munich, Fed. Rep. of Germany

[21] Appl. No.: 712,833

[22] Filed: Jun. 10, 1991

[30] Foreign Application Priority Data

Jun. 8, 1990 [DE] Fed. Rep. of Germany ....... 4018441

[51] Int. Cl.$^5$ ...................... C12N 15/55; C12N 15/63; C12N 9/22; C12N 9/10
[52] U.S. Cl. ................................. 435/172.3; 435/193; 435/199; 435/252.3; 435/252.33; 435/320.1; 536/27
[58] Field of Search .................... 435/193, 199, 172.3, 435/320.1, 252.3, 252.33; 536/22

[56] References Cited

FOREIGN PATENT DOCUMENTS 0193413 9/1986 European Pat. Off. .
0248678 12/1987 European Pat. Off. .

OTHER PUBLICATIONS

Gene, vol. 94, No. 1, Sep. 1990, "Cloning, expression and characterization of the Sau3AI restriction and modification genes in *Staphylococcus carnosus* TM300", pp. 37–43.
Nucleic Acids Research, vol. 3, No. 11, Nov. 1976, "A restriction endonuclease from Staphylococcus aureus", pp. 3193–3202.
Journal of Bacteriology, vol. 164, No. 2, Nov. 1985, "Cloning of a Restriction-Modification System from *Proteus vulgaris* and Its Use in Analyzing a Methylase-Sensitive Phenotype in *Escherichia Coli*", pp. 501–509.
Biokhimiya, vol. 54, No. 6, Jun. 1989, "DNA Methylase Sau 3A Isolation and Properties", pp. 1009–1014, abstract only.
Gene, vol. 74, 1988, "Cloning type-II restriction and modification genes", pp. 25–32.

*Primary Examiner*—Charles L. Patterson, Jr.
*Attorney, Agent, or Firm*—Nikaido, Marmelstein, Murray & Oram

[57] ABSTRACT

The invention concerns a DNA which contains
(1) at least one of the two regions of the nucleotide sequence SEQ ID NO:1 coding for a protein with a Sau3AI methylase activity or for a protein with a Sau3AI endonuclease activity.
(2) a sequence corresponding to the DNA from (1) within the scope of the degeneration of the genetic code or
(3) a sequence which hybridizes under stringent hybridization conditions with a DNA from (1) or (2).

In addition a vector is disclosed which contains a DNA according to the present invention, in particular under the control of a regulatable closed promoter, as well as microorganisms which are transformed with one or several vectors according to the present invention and the isolation of recombinant Sau3AI endonuclease from the transformed microorganisms.

27 Claims, 6 Drawing Sheets

RECOMBINANT RESTRICTION ENZYME SAU3AI

DESCRIPTION

Restriction modification (R-M) systems of the classes I, II and III in bacteria represent defence mechanisms against invading DNA molecules. They consist of two enzymatic activities:

1. a restriction endonuclease which recognizes and cleaves non-modified and thus unprotected DNA at a specific recognition site and
2. a DNA modification-methyl transferase which protects the cellular DNA against cleavage by the restriction endonuclease by a specific methylation of at least one special base in the same sequence.

In this way the various R-M systems enable the bacterium to be resistant against a phage infection. This phage resistance was the basis for the development of an international phage classification system for *Staphylococcus aureus* (Williams and Rippon, J. Hyg. 50 (1952), 320–353) in order to characterize different strains of *S. aureus*. According to their phage classification, *S. aureus* strains can be divided into four groups. The differences between the individual groups are mainly a result of the R-M activity. Sussenbach et al. (Nucleic Acids Res. 3 (1976), 3193–3202) were able to isolate the class II restriction enzyme Sau3AI (or R.Sau3AI) from the group II strain *S. aureus* 3AI. It recognizes the palindrome sequence 5'-GATC-3' and cleaves in front of the G residue on each DNA strand. The Sau3AI methyl transferase (M.Sau3AI) modifies the C residues of both strands at position $^5$C so that a sequence 5'-GAT$^{5\text{-}Me}$C-3' is formed which cannot be cleaved by the restriction enzyme.

The restriction enzyme Sau3AI has been known for many years. It is isolated from *Staphylococcus aureus* 3A and has proven to be one of the most important restriction enzymes for recombinant DNA technology (e.g. in connection with BamHI (5'-G/GATCC-3') for the production of gene banks). The methylase M.Sau3AI which has not been obtainable up to now could also be of great interest for the methylation of DNA.

The isolation of Sau3AI causes problems and high costs in as much as the host organism *S. aureus* is pathogenic and difficult to lyse which is a considerable impediment to the isolation of the enzyme. In addition *S. aureus* has also interfering side activities which additionally hinder the purification and isolation of the enzyme.

Thus there is a great necessity to clone the restriction modification system Sau3AI in a more suitable organism and to express it there in order to enable an improved isolation of the restriction enzyme. The organism which would be best for this is the gram-negative bacterium *E. coli*.

There are many known processes for cloning restriction modification systems from different organisms in *E. coli* which are described by Wilson (Gene 74 (1988, 281–288). These processes include e.g. the subcloning of natural plasmids on which the genes of a R-M system are located or a selection based on phage restriction. However, usually a selection strategy is used in which a gene bank of genomic DNA fragments of the original organism is set up in *E. coli* and an in vitro selection for methylase-positive clones is carried out. Already more than 50 modification genes have been isolated in this way, many of which together with the corresponding restriction gene in each case, which in general is located directly next to the methylase gene. However, it is not possible to clone the Sau3AI R-M system using these known processes.

The object of the present invention was to overcome these difficulties and to find a possibility for cloning and expressing the restriction enzyme Sau3AI.

The object according to the present invention is achieved by the provision of a DNA which contains (1) at least one of the two regions of the nucleotide sequence SEQ ID NO:1 coding for a protein with a Sau3AI methylase activity or for a protein with a Sau3AI endonuclease activity.

(2) a sequence corresponding to the DNA from (1) within the scope of the degeneration of the genetic code or (3) a sequence which hybridizes under stringent hybridization conditions with a DNA from (1) or (2).

Surprisingly the cloning of the genes of the Sau3AI restriction modification system is successful when a host organism is used which is closely related to *S. aureus* 3AI but does not possess the Sau3AI restriction modification system. The non-pathogenic bacterium *Staphylococcus carnosus*, DSM 5875, however, without plasmid (Schleifer and Fischer, Int. J. Syst. Bact. 32 (1982), 153–156; Götz et al., Plasmid 9 (1983)) is preferably used as the organism which is closely related to *S. aureus*. Further suitable strains for cloning the Sau3AI R-M system are e.g. *Staphylococcus xylosus* C2A and different *Staphylococcus aureus* strains from *S. aureus* 3AI, which do not contain the Sau3AI R-M system. In this way it is possible to obtain a DNA according to the present invention which completely contains both genes of the Sau3AI R-M system.

A recombinant vector which contains a DNA according to the present invention with both genes of the Sau3AI R-M system is the plasmid pSEM7 (FIG. 1). *Staphylococcus carnosus*, transformed with the plasmid pSEM7, was deposited at the DSM under the number 5875. Fragments with the incomplete genes of the Sau3AI R-M system were cloned in the *E. coli* vector pUC19. Their nucleotide sequence was determined according to the dideoxy method of Sanger.

The nucleotide sequence of Sau3AI R-M system shows two large open reading frames which are transcribed in the same direction (SEQ ID NO:1). The genes for the Sau3AI methylase and for the Sau3AI restriction endonuclease can be unambiguously localized on the basis of mapping and protein sequencing data. R.Sau3AI is coded by an open reading frame which extends from base 448 to base 1914. M.Sau3AI is coded by the open reading frame which begins at base 2017 and ends at base 3252.

The Sau3AIR gene begins with the start codon TTG. The identity of and the translation start of the Sau3AIR reading frame were confirmed by sequencing the first 23 N-terminal amino acids of the purified enzyme. Accordingly R.Sau3AI consists of 489 amino acids with a calculated molecular weight of 56.5 kD. This corresponds to the migration behaviour of purified R.Sau3AI in SDS PAGE.

The reading frame of the Sau3AI M gene codes for a protein with 412 amino acids with a calculated molecular weight of 47.3 kD. Both genes of the R-M system have a G+C content of 31%.

In this way the Sau3AI methylase activity could be subcloned alone on a 3.7 kb EcoRV fragment. The resulting plasmid pTSMI is 8.4 kb long and also carries a short inactive fragment of the endonuclease gene apart from the active methylase gene (see FIG. 2).

The *S. carnosus/E. coli* shuttle vector pBT-SM11 (see FIG. 3) could be produced by insertion of a 2.3 kb fragment (EcoRI, PvuII, blunt ends by treatment with Klenow enzyme) of the *E. coli* vector pBR322 into the SalI cleavage site (also with blunt ends by treatment with Klenow) of pTSM1. It causes an undiminished Sau3AI methylase activity in *S. carnosus*. However, retransformation experiments in *E. coli* resulted in a substantial interference of the Sau3AI methylase acitivity by *E. coli* enzymes which prevents the direct cloning of the original Sau3AI methylase in *E. coli*.

Surprisingly, it was nevertheless possible to obtain a methylase-positive *E. coli* clone. This was achieved by a targeted mutation in the methylase gene in which only one base was exchanged, so that an altered gene was obtained which hybridizes with the original gene under stringent conditions. A plasmid which contains the gene altered by mutation can be transferred back and forth between *E. coli* and *S. carnosus* without loss of the methylase activity.

The active mutated methylase gene could also be incorporated as a SacI/XbaI fragment into the multiple cloning site of pUC18 and successfully transformed in different *E. coli* K12 strains.

In the mutated methylase gene which is active in *E. coli* the cytosine at position 2134 of the DNA sequence SEQ ID NO:1 is converted into a thymidine by site-directed mutagenesis. This mutation causes a conversion of an arginine codon (CGA) into an opal stop codon (TGA). It is thus a nonsense mutation in the reading frame of the Sau3AIM gene which results in a reduction of the gene expression but reduces the incompatibility of the Sau3AI methylase with *E. coli* to such an extent that the mutated gene can be cloned without difficulty in *E. coli*. Surprisingly a certain methylase level is still present in the cells transformed with the mutated gene since the gene causes the *E. coli* DNA to be resistant against digestion by Sau3AI.

The present invention also provides a DNA which codes for a protein with Sau3AI methylase activity which can be expressed in *E. coli*. This DNA has preferably a nucleotide sequence which is modified compared to the wild-type such that a Sau3AI methylase protein formed from it by transcription and translation has a reduced methylase total activity compared to the wild-type. Such a modified gene can differ from the wild-type in that one or several mutations are introduced within or/and outside of (e.g. promoter or ribosomal binding site) the coding region of the Sau3AI methylase gene which results in a better toleration of the gene in the respective host organism, preferably in *E. coli*.

Generally suitable in the sense of the invention are modifications (i.e. substitutions, deletions or incorporation of additional bases) in the region of the Sau3AI M gene (i.e. in the gene or in its neighbourhood) which cause a reduction in the total activity of methylase in the cell by reducing the expression level or/and the specific activity of this protein. These also include e.g. deletions of larger DNA fragments of the coding sequence or/and fusions with other proteins or polypeptides whereby the specific methylase activity of the protein is reduced.

In this connection methylase mutants are preferably suitable which contain a stop codon in the coding region of the gene, particularly preferably within the first 1000, most preferably within the first 500 bases, which is preferably followed by at least one A residue. Suitable stop codons are e.g. opal stop codons. Such mutations result in a reduction in the expression rate of the methylase gene in *E. coli* of 90 to 95%.

The object of the present invention was an improved expression of the Sau3AI endonuclease. Thus a further subject matter of the present invention is also a recombinant vector containing one or several copies of a DNA according to the invention which in particular codes for the Sau3AIR gene. The recombinant vector according to the present invention is preferably suitable for multiplication in prokaryotic organisms. In this connection it can be a vector which is present extrachromasomally (e.g. plasmid) or a vector which is integrated into the host genome (e.g. bacteriophage λ). The vector according to the present invention is preferably a plasmid. The recombinant vector according to the present invention especially preferably contains an origin of replication which is active in *E. coli* i.e. it can be multiplied in *E. coli*.

Most preferred is a recombinant vector on which the Sau3AI, endonuclease gene is located under the control of a regulatable promoter. The own promoter of the Sau3AIR gene must be inactive for this e.g. by a deletion up to a few nucleotides before the ribosomal binding site. The regulatable promoter must be very tightly "closed", i.e. if possible no transcription should take place under repression conditions since the Sau3AI endonuclease represents a very toxic protein for the cell. Suitable regulatable and "closed" promoters are e.g. the fdhF promoter (EP-A-0 285 152), the pdoc promoter in *E. coli* JM83 with the lysogenic phage lambda (O'Connor and Timmis, J. of Bacteriol. 169 (1987), 4457–4462) or a T7 promoter which can be located on a "high copy" plasmid (e.g. pUC 18), in combination with a chromosomal T7-RNA polymerase gene under the control of the inducible lac UV5 promoter and the T7 lysozyme gene (T7 lysozyme is a specific inhibitor for the T7-RNA polymerase) on an additional plasmid, e.g. pLys5 (Studier and Moffat, J. Mol. Biol. 189 (1986), 113 ff; Moffat and Studier, Cell 49 (1987), 221–227).

A vector according to the present invention for the recombinant expression of the Sau3AI endonuclease preferably also contains at least one transcription terminator 5'-upstream of the Sau3AIR gene in order to prevent to as large an extent as possible a "reading through" of a gene located 5'-upstream. The λT$_0$ terminator (Schwarz et al., Nature 272 (1978), 410–414) has for example proven to be well suited. Other strong terminators (which are familiar to one skilled in the art) can, however, also be used.

The present invention also provides a microorganism which is transformed with the DNA according to the present invention or with one or several recombinant vectors according to the present invention.

In this connection of course, on the one hand, microorganisms are suitable which originally, i.e. before transformation with the vector or with the vectors according to the present invention, did not contain the genes of the Sau3AI R-M system. On the other hand, for this purpose one can also transform a *S. aureus* 3AI producer strain which is usually used for obtaining the Sau3AI endonuclease and already contains the Sau3AI R-M system, with a vector (e.g. pSEM7) according to the present invention which is suitable for Staphylococci. A substantially improved expression of R-Sau3AI is possible using the latter method in which the problems which occur when lysing Staphylococci are also reduced.

The intermediate cloning strain S. carnosus, transformed with pSEM7 (DSM 5875), is for example suitable as the microorganism which does not originally contain a Sau3AI R-M system.

However, microorganisms of the E. coli, Pseudomonas and Bacillus strains, in particular E. coli, are preferred as the host organism for a vector according to the present invention. When using such a microorganism attention must be paid to the fact that the Sau3AIR gene without a protecting methylase is extremely toxic for the organism.

In a preferred embodiment of the present invention the microorganism is therefore transformed with a recombinant vector which contains a DNA which codes for a protein with a Sau3AI methylase activity which is tolerated by the respective microorganism used in each case as well as for a protein with Sau3AI endonuclease activity. In this way it is possible to achieve a recombinant expression of the Sau3AI restriction enzyme in the transformed organism since besides the Sau3AI endonuclease gene an active Sau3AI methylase gene is present at the same time which protects the DNA of the host organism against cleavage. If a microorganism such as e.g. E. coli is used in which the methylase wild-type gene is not expressible, then a suitable mutated methylase gene (see above) is used.

In a further preferred embodiment the microorganism is transformed with two mutually compatible vectors i.e. the microorganism contains two vectors with different origins of replication which can be permanently present together in the transformed cell. One of these vectors contains a DNA which codes for a protein with Sau3AI methylase activity which is tolerated by the respective microorganism used in each case. Thus the DNA of the transformed microorganism is already present in a methylated form when the microorganism is transformed with the second vector which is compatible with the first vector and which contains a DNA which codes for a protein with Sau3AI endonuclease activity. In this way a recombinant expression of the Sau3AI restriction enzyme in transformed microorganisms e.g. E. coli, is possible. The choice of suitable compatible vectors is left up to one skilled in the art, e.g. a suitable vector system for E. coli can contain a vector with a ColE1 origin of replication (such as e.g. pBR322) and a second vector with a p15A origin of replication (Chang and Cohen J. Bacteriol. 134 (1978), 1141-1156).

A generally preferred alternative for the transformation of the Sau3AI-R gene in a host organism is to use a vector on which the Sau3AI gene is located under the control of a regulatable "closed" promoter (see above). The use of a regulatable closed promoter is absolutely essential in the absence of a methylase gene and is, however, also to be recommended when a methylase gene which is tolerated by the cell is present. Thus, e.g. in order to further reduce the toxicity of the Sau3AI endonuclease for the cell, the microorganism can be additionally transformed with a compatible vector which contains a methylase gene which is tolerated by the respective microorganism and is mutated if desired.

In addition the invention also encompasses a process for the isolation of a DNA which codes for a protein with Sau3AI methylase activity or/and for a protein with Sau3AI endonuclease activity in which one produces (1) a gene bank of chromosomal DNA fragments of an original organism which has the Sau3AI restriction modification system by transformation of an organism which is closely related to the original organism and which does not originally have a Sau3AI restriction modification system,
(2) clones of the transformed organism are tested for Sau3AI methylase activity and
(3) positive clones with Sau3AI methylase activity are isolated therefrom which in addition contain a gene which codes for a protein with a Sau3AI endonuclease activity.

By this means it is possible to isolate the genes for the Sau3AI R-M system. Preferably Staphylococcus aureus 3AI is used as the original organism and Staphylococcus carnosus, Staphylococcus xylosus C2A or different Staphylococcus aureus strains of S. aureus 3AI are used as the organism which is closely related to the original organism. S carnosus, DSM 5875 (without the plasmid pSEM7) is especially preferred. In order to produce the gene bank of the original organism one uses a suitable vector which can be replicated in the organism which is closely related to the original organism. The production of a S. aureus gene bank in a suitable vector and the transformation of the organism closely related to S. aureus with the recombinant vector can be carried out by means of techniques which are known to one skilled in the area of molecular biology. It is essential for the invention that the closely related organism does not contain a Sau3AI restriction modification system since otherwise a selection for positive clones would not be possible.

The plasmid pCA44 (FIG. 5), a 4.4 kb long ScaI/PvuII deletion derivative of pCA43 (Kreutz and Götz, Gene 3 (1984), 301-304) in which the partially cleaved chromosomal DNA of S. aureus 3AI has been incorporated can serve for example as the cloning vector for the process according to the present invention. A gene bank obtained by transformation of S. carnosus, DSM 5875 (without plasmid pSEM7) as protoplasts with the cloning vector is then tested for Sau3AI methylase activity. For this one preferably incubates plasmid preparations from the clones of the gene bank with commercial Sau3AI and examines the preparations electrophoretically. A clone which expresses the Sau3AI methylase gene is namely resistant to a restriction cut by Sau3AI. Methylase-positive clones are isolated and tested again.

Two clones were obtained in this way with methylase activity. Sau3AI endonuclease activity could also be detected in the crude extract of these two clones. The recombinant plasmids were isolated from both clones and a restriction map was made from the smaller of the two. This 14.3 kb plasmid pSEM7 (FIG. 1) contains both genes of the Sau3AI RM system on a 9.6 kb insertion.

Figure 4:
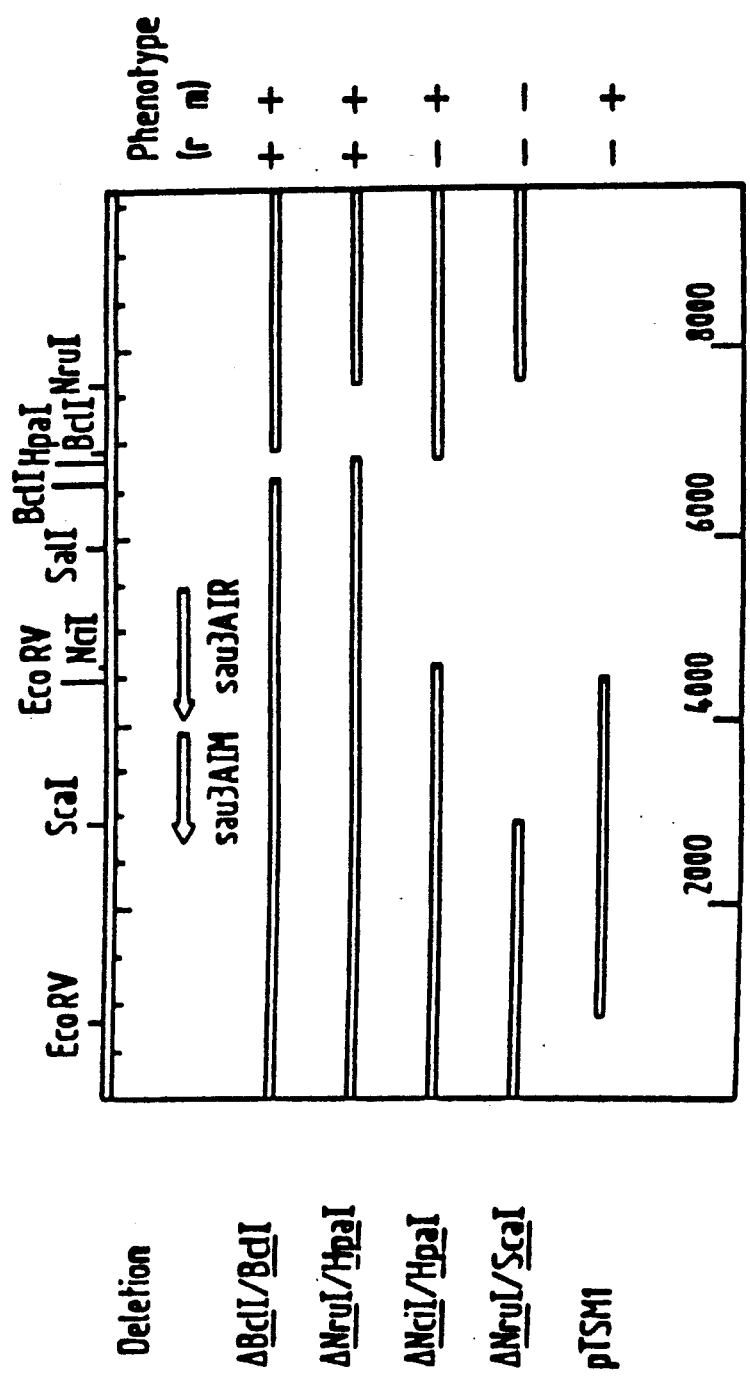

A restriction map of the insertion of the plasmid pSEM7 was determined and the localization of the endonuclease and methylase genes was established by construction of different deletions and subclones (FIG. 4). By this means not only the localization of the R-M genes on the plasmid pSEM7 was established but it was also found that both genes have their own promoter.

Therefore one can obtain the DNA coding for the Sau3AI R-M system by the method described above. The present invention encompasses in addition a process for the isolation of a recombinant DNA according to the present invention which can also be expressed in the target organism in which per se the expression of the Sau3AI methylase wild-type gene is not possible. This can be carried out by specifically introducing mutations outside (promoter, ribosomal binding site) or/and within the coding region of the Sau3AI methylase gene by well known techniques (e.g. in vitro mutagenesis) which allow an expression of the Sau3AI methylase in the target organism. The type of mutations used was already described in detail above.

In this way a Sau3AI methylase gene is obtained which can be expressed in a desired target organism, preferably E. coli. Such a gene especially preferably has an opal stop codon in the coding region in contrast to the wild-type gene, preferably in the first 1000, particularly preferably in the first 500 bases of the methylase gene, which is directly followed by an A residue.

The invention also includes a process for the isolation of a recombinant protein with Sau3AI endonuclease activity in which a microorganism transformed with one or several recombinant vectors according to the present invention, in which at least one copy of a Sau3AI endonuclease gene must be present on one of the vectors, is cultured in a medium which is suitable for the respective microorganism and under appropriate expression conditions and the protein is isolated from the cell extract or medium.

In this process a prokaryotic microorganism is preferably used as the host organism. This can be on the one hand a microorganism which originally does not possess a Sau3AI restriction modification system. E. coli, Bacillus or Pseudomonas, particularly preferably E. coli, may be mentioned as examples in this case. The Sau3AI restriction enzyme can, however, also be isolated from Staphylococcus carnosus, DSM 5875 (without pSEM7) which is transformed with a vector which contains the Sau3AI R-M system (e.g. pSEM7). In the process for isolating the Sau3AI endonuclease from a recombinant host organism it is particularly preferred that the endonuclease gene is introduced under the control of a regulatable closed promoter and, if desired, together with a methylase gene which is tolerated by the respective host organism. This methylase gene can be located on the same vector as the endonuclease gene. It can, however, also be present on a further vector (intrachromosomal or extrachromosomal). It is possible by expression control with the aid of a regulatable closed promoter or/and by protecting the cellular DNA from cleavage in the presence of a methylase gene to isolate recombinant Sau3AI endonuclease from transformed host cells.

When a Sau3AI endonuclease gene under the control of a regulatable closed promoter is used, it is expedient to first culture the microorganisms in a repressed state (i.e. no expression of the Sau3AIR gene takes place) and then an induction step is carried out which causes a high expression of the Sau3AI endonuclease within a short time.

On the other hand one can, however, also transform the S. aureus strain 3AI usually used for the isolation of the Sau3AI endonuclease with a vector which contains the Sau3AI endonuclease gene and, if desired, also the Sau3AI methylase gene. Such a transformed S. aureus 3AI strain is just as well suited for the isolation of the Sau3AI endonuclease since the purification of the enzyme is considerably simplified by the increased expression of the endonuclease gene coded by the plasmid.

Thus by means of the process according to the present invention, a high expression of the Sau3AI restriction enzyme is possible in different organisms which, such as e.g. E. coli, are not pathogenic and easy to lyse and which do not produce interfering side activities. In this way the process according to the present invention succeeds in substantially reducing the production costs for the restriction enzyme Sau3AI which is important for molecular biology.

Thus, the present invention also provides a recombinant protein with Sau3AI endonuclease activity which is obtained from an organism which has been transformed with one or several recombinant vectors according to the present invention and, if desired, originally did not contain a Sau3AI restriction modification system.

Finally the present invention also includes a protein with Sau3AI methylase activity which is encoded by a DNA according to the present invention. The isolation of a Sau3AI methylase is possible from S. carnosus, DSM 5875 (without plasmid) which is transformed with a suitable vector such as pTSM1 containing the methylase gene. An isolation of the wild-type Sau3AI methylase from E. coli is possible when the gene coding for this is under the control of a regulatable closed promoter. The isolation of a modified methylase which is tolerated by E. coli is possible by subcloning in the usual way.

Finally the invention also includes a reagent for the restriction cleavage of DNA which contains a recombinant Sau3AI endonuclease which was isolated from an organism transformed with one or several vectors according to the present invention.

The following microorganisms and plasmids were deposited at the German Collection for Microorganisms, Mascheroder Weg 1b, D-3300 Braunschweig:
1) pBN 208 with the depositary number DSM 4069p on 27, Mar. 1987
2) Staphylococcus carnosus, transformed with the plasmid pSEM7 with the depositary number DSM 5875 on 17, Apr. 1990

The following examples in conjunction with the sequence protocol and the FIGS. 1 to 7 are intended to elucidate the invention.

Figure 2:
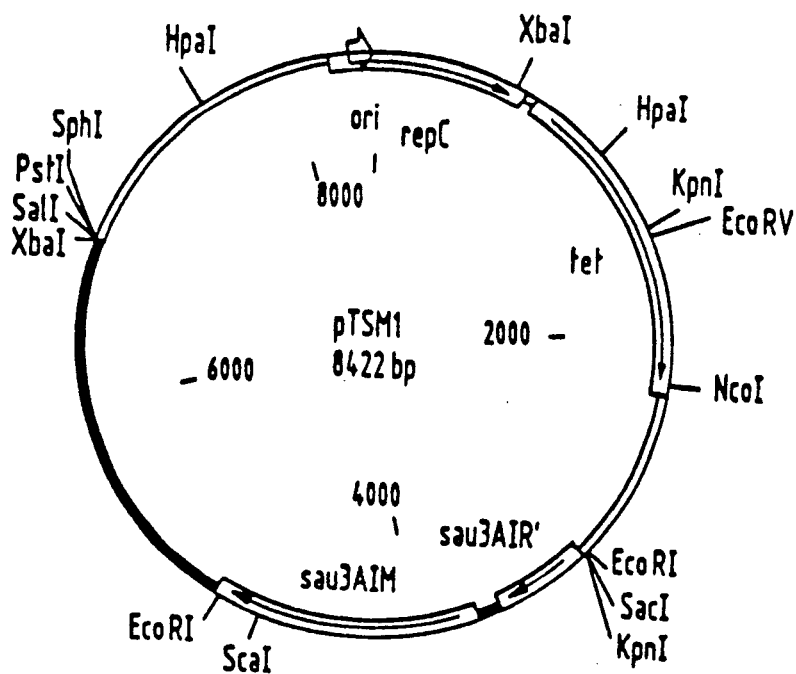
Figure 3:
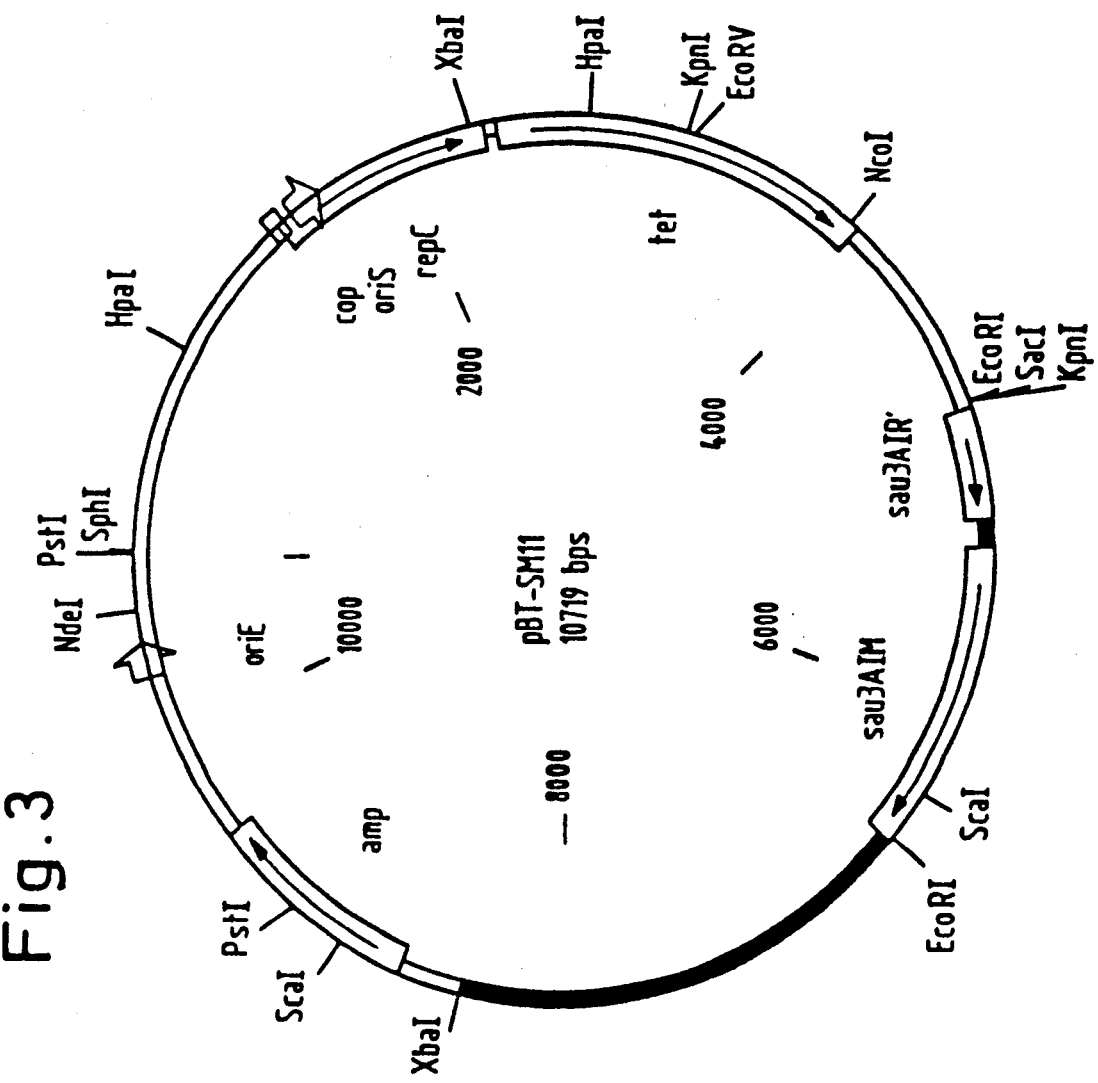
Figure 5:
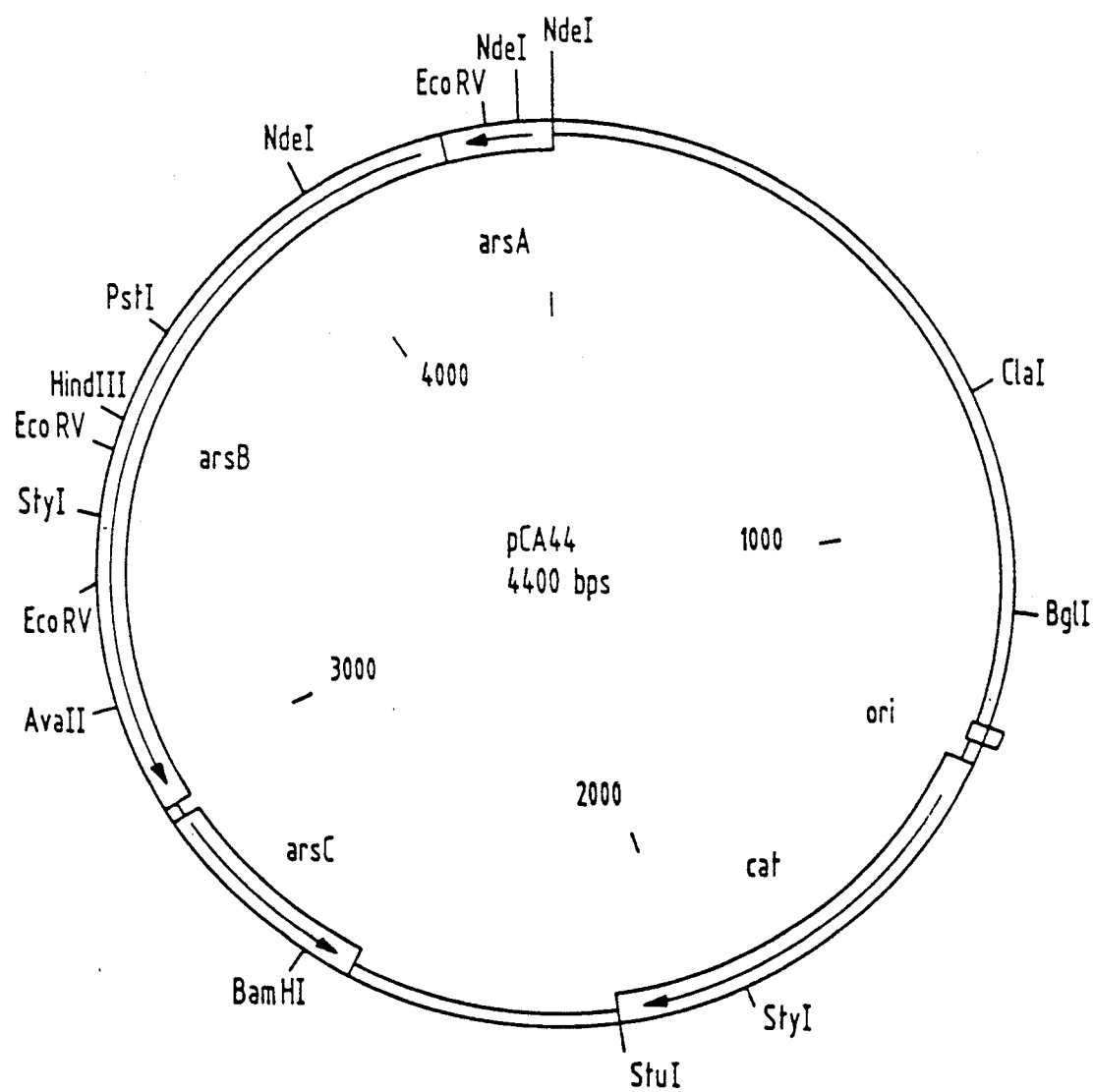
Figure 6:
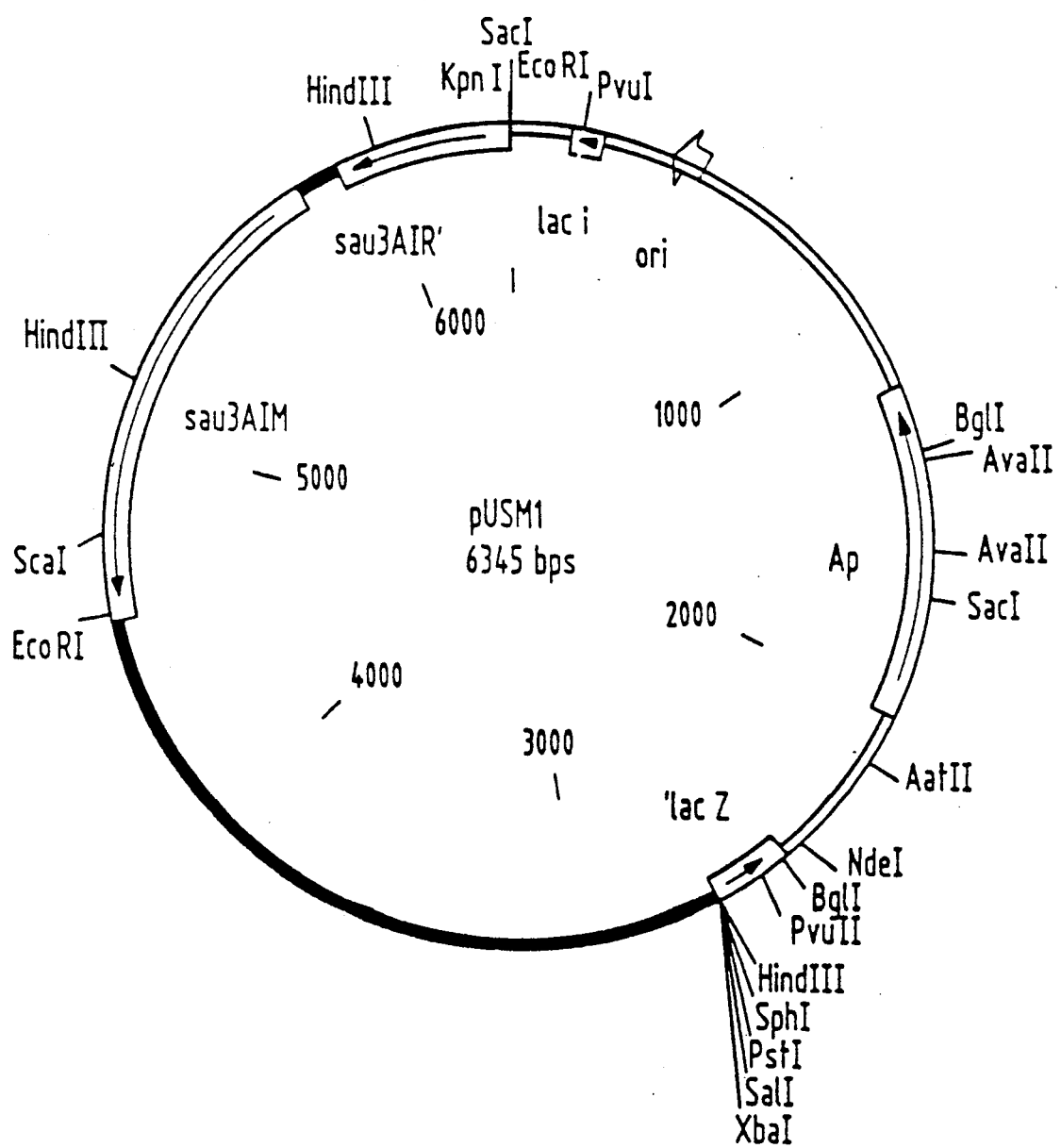
Figure 7:
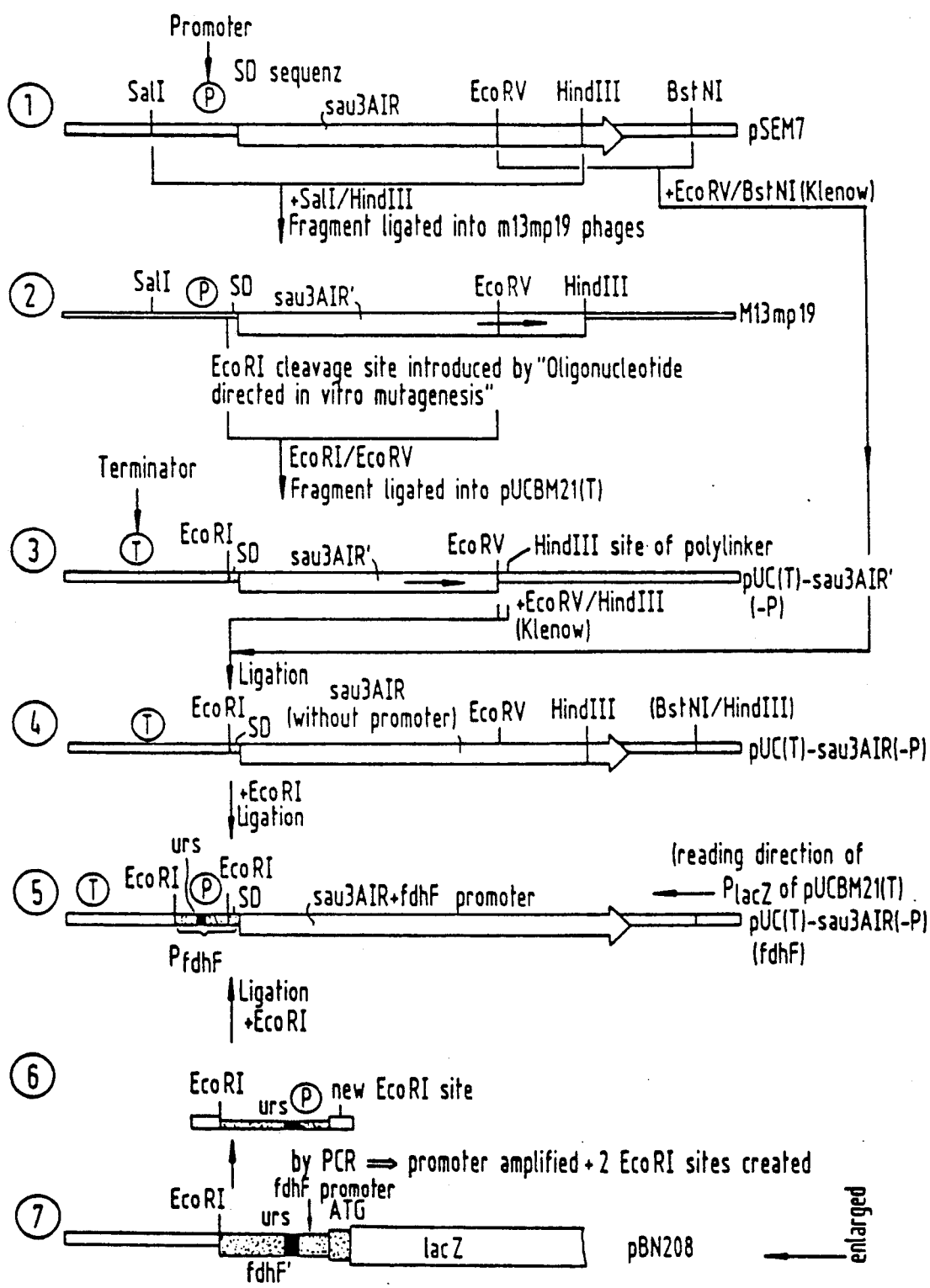

SEQ ID NO:1 shows the nucleotide and amino acid sequence of the genes for the Sau3AI restriction modification system, FIG. 1 shows the plasmid pSEM7, FIG. 2 shows the plasmid pTSM1, FIG. 3 shows the plasmid pBT-SM11, FIG. 4 shows the production of deletions and subclones for the characterization of the insertion of pSEM7, FIG. 5 shows the plasmid pCA44, FIG. 6 shows the plasmid pUSM 1, FIG. 7 shows the construction of a Sau3AI expression vector for E. coli.

EXAMPLE 1

Cloning of the Sau3AI R-M system 1.1 Production of S. aureus DNA fragments and ligation into a vector.

A BM medium with the following composition was used for the culture of Staphylococci:

| | |
|---|---|
| Tryptone | 10 g |
| Yeast extract | 5 g |
| NaCl | 5 g |
| Glucose | 1 g |
| $K_2HPO_4$ | 1 g |
| $H_2O$ dist. | ad 1 l | pH 7.2

10 μg/ml chloramphenicol is added to the medium for the culture of pCA44, pSEM7 in *S. carnosus*, DSM 5875 (without plasmid). 20 μg/ml tetracycline is added to the medium for the culture of pTSM1, pBT-SM11 in *S. carnosus*, DSM 5875 (without plasmid).

Plasmid DNA and chromosomal DNA from *S. aureus* were isolated by the clear-lysate method (Novick and Bouanchand, Ann. N.Y. Acad. Sci. 182 (1971), 279-291).

Procedure for the plasmid preparation:

Inoculate 1 to 1.5 l BM medium in 5 l Erlenmeyer flask (with corresponding antibiotic) with the preculture and incubate at 37° C. until the end of the exponential phase (ca. 12 to 18 hours);

centrifuge the cells and wash with 40 ml EDTA wash solution (0.15 mol/l EDTA, pH 8.0).

Resuspend in 60 ml NaCl buffer (0.05 mol/l Tris/HCl; 2.5 mol/l NaCl; 0.05 mol/l EDTA; pH 8.0) and transfer to a 250 ml Erlenmeyer flask;

add 1 to 1.5 ml lysostaphin (Sigma) solution (0.5 mg/ml) and incubate at 37° C. while shaking gently until the suspension adopts a slimy, viscous consistency (after 15 to 25 minutes);

mix with 60 ml ice-cold lysis buffer (0.05 mol/l Tris/-NaOH; 0.3 mol/l EDTA; 0.5% Brij 58, 0.04% Na deoxycholate; pH 8.0) and place on ice for one hour.

Centrifuge at 27500 g, 4° C., 20 minutes;

carefully decant the supernatant (the pellet is often very soft) and precipitate with 30 ml 50% PEG (PEG 6000) for 2 hours at 4° C.;

centrifuge at 8000 g, 4° C., 20 minutes;

decant the supernatant and carefully dissolve the glassy, opaque pellet in 10 ml TE buffer (10 mmol/l Tris, 1 mmol/l EDTA, pH 8);

add a spatula tip of proteinase K (Serva). Incubate at 37° C. for 15 minutes while shaking gently;

purify by CsCl density gradient centrifugation.

A slight modification of the plasmid isolation protocol has proven to be the most expedient method for the preparation of chromosomal DNA from Staphylococci. The only difference to the method described above is that the suspension is shaken thoroughly from time to time during the one hour lysis in order to enable the release of high molecular DNA from the cells and to increase the yield of chromosomal DNA. After the ethanol precipitation the DNA should be wound onto a glass rod and subsequently dissolved in TE buffer. Centrifugation should be avoided because of the poor solubility of agglomerated, chromosomal DNA.

The chromosomal *S. aureus* 3AI DNA was partially cleaved with MboI. Fragments in the size range of 7 to 15 kb were isolated by means of an agarose gel. These fragments were ligated into the vector pCA44 (FIG. 5) which had been cleaved with BamHI and treated with alkaline phosphatase, a 4.4 kb ScaI/PvuII deletion derivative of pCA43 (Kreutz and Götz (1984), supra).

1.2 Production of a *S. aureus* gene bank in *Staphylococcus carnosus*, DSM 5875 (without plasmid) The transformation of *S. carnosus* with the ligated vector from 1.1 was carried out with polyethylene glycol induced protoplast fusion as described by Götz and Schumacher (FEMS Letts. 40 (1987), 285-288).

Procedure:

a) Production of protoplasts

Inoculate 6×300 ml BM medium with 1.5 ml in each case of a 12 hour culture of *Staphylococcus carnosus*, DSM 5875 (without plasmid);

allow to grow until an OD 578 of 0.4 to 0.5;

centrifuge the cells in sterile, screwable, plastic beakers at 3300 g, 4° C., for 20 minutes;

suspend each of the cell sediments in 30 ml SMMP (see Götz and Schumacher (1987), supra) and transfer to sterile 100 ml flasks;

add 20 μl sterile-filtered lysostaphin solution (0.5 mg/ml);

allow the flasks to stand for 12 to 16 hours at 30° C.;

monitor the formation of protoplasts in a light microscope (the cells should be single, enlarged and not lysed);

centrifuge the propoplasts in sterile plastic screw-cap tubes (40 ml) at 4000 g and room temperature for 25 minutes;

wash the cells with 5 ml SMMP;

dissolve the sediment in 2 ml SMMP and divide up into 300 μl portions in sterile screw-cap tubes; storage is only possible at −70° C.

b) Protoplast transformation slowly thaw 300 μl protoplast suspension;

add transforming DNA solution;

immediately add 2 ml PEG 6000 (40%) in SMM (2x SMM: 1 mol/l saccharose, 40 mmol/l maleic acid, 40 mmol/l $MgCl_2$, pH 6.8) and mix carefully;

after 2 minutes stop the transformation by addition of 7 ml SMMP (8 parts 2x SSM, 2 parts 4x PAB (Difco antibiotic medium), 370 g/l, 0.5 parts 5% BSA);

centrifuge down (4000 g, room temperature, 25 minutes);

resuspend the sediment by carefully shaking in 1 ml SMMP;

plate 100 to 200 μl of the protoplast suspension on DM-3 plates (Götz and Schumacher, FEMS Letters 40, 1987, 285-288); when transforming with intact plasmids dilute ($10^3$- to $10^6$-fold);

incubate the plates for 3 to 4 hours at 37° C. in order to regenerate the cell walls and for the phenotypic expression of the resistance characteristics;

cover each of the plates with 3 ml CY-3 Agar containing inhibitor (Götz and Schumacher, FEMS Letters 40, 1987, 285-288); add the inhibitor in a 10-fold concentration (chloramphenicol 100 μg/ml, tetracycline 200 μg/ml; in 30 ml DM-3 Agar because of dilution by diffusion);

incubate for 2 days at 37° C.

1.3 Isolation of M.Sau3AI- and R.Sau3AI-active clones

The DNA isolation from *S. carnosus* was carried out on a large scale according to Götz et al., (Plasmid 9 (1983), 126-137), the mini-preparations were essentially carried out according to the alkaline lysis standard method according to Birnboim and Doly (Maniatis et al., (1982), Molecular Cloning. A Laboratory Handbook), except that before lysis with NaOH/SDS the cells were incubated with 8 to 12 μg/ml lysostaphin for 10 minutes at 37° C.

The M.Sau3AI activity of recombinant *S. carnosus* clones was determined by the simultaneous testing of 5 clones in each case whereby the isolated plasmids were cleaved with Sau3AI and the cleaved DNA was examined by agarose gel electrophoresis.

The DNA from clones expressing M.Sau3AI was resistant to cleavage by commercial Sau3AI endonuclease. The clones from the M-positive preparations were separated and tested again individually.

The M-active clones were tested for R activity by incubation of 1 μl of the crude extract (produced by treating the cells twice in a French press with 16000 psi) with 1 μg pBR322 for one hour at 37° C. After agarose gel electrophoresis the restriction pattern was examined. pBR322 which was cleaved with commercial Sau3AI served as a control.

Two out of approximately 800 tested transformants showed resistance against Sau3AI cleavage as a result of the expression of a cloned Sau3AI methylase gene. These two recombinant plasmids pSEM7 and pSEM11 both showed the same resistance to Sau3AI cleavage as the chromosomal DNA of S. aureus 3AI. Both clones showed M.Sau3AI activity as well as R.Sau3AI activity.

1.4 Characterization and sequence analysis of positive clones

The smaller recombinant plasmid pSEM7 (FIG. 1) contains a 9.6 kb insertion. A restriction map of this plasmid was produced and the localization of the endonuclease and the methylase gene was determined by the production of different deletions and subclones (FIG. 4). The BclI/BclI and the NruI/HpaI deletions had no influence on the R-M activity, while the NciI/HpaI and the NruI/ScaI deletions led to the loss of R activity or of both activities. The Sau3AI methylase gene was cloned on a 3.66 kb long EcoRV fragment into the SmaI site of the plasmid pT18Imcs, a derivative of pT18I (Khan and Novick, Plasmid 10 (1983), 251–259), which contains the PvuII fragment with the multiple cloning sequence (mcs) of pUC18 inserted in the NdeI site. The resulting plasmid pTSMI is 8.4 kb long and still carries a short inactive fragment of the endonuclease gene apart from the active methylase gene (FIG. 2).

The nucleotide sequence of the gene of the Sau3AI R-M system was determined according to the dideoxy-DNA sequencing method according to Sanger. The result of the sequence analysis is shown in the sequence protocol (SEQ ID NO:1).

EXAMPLE 2

Isolation of Sau3AI methylase genes which can be expressed in E. coli

The S. carnosus/E. coli shuttle vector pBT-SM11 (FIG. 3) could be produced by insertion of a 2.3 kb fragment (EcoRI/PvuII, blunt ends by Klenow treatment) of the E. coli vector pBR322 (with origin of replication and β-lactamase gene) into the SalI cleavage site (also with blunt ends by Klenow treatment) of pTSMI (FIG. 2, Example 1.4). It causes undiminished Sau3AI methylase activity in S. carnosus.

Procedure for the recloning experiments:

The shuttle vector pBT-SM11 was cloned in S. carnosus, DSM 5875 (without plasmid), isolated and 0.2 μg plasmid DNA was used in each case for recloning experiments. The E. coli cells were made competent according to the CaCl$_2$ method. The transformation experiments were carried out according to standardized methods:

200 μl cells from 1 ml competent E. coli cells were used for the transformation.

100 μl portions from 1.3 ml transformed cells were plated on BM agar plates.

Commercially obtainable E. coli K12 strains (e.g. JM83, JM109) were used as test strains.

An extremely low transformation rate was obtained with pBT-SM11 in all tested E. coli strains.

Procedure for the in vitro mutagenesis:

A mutagenesis of the Sau3AI methylase gene was carried out starting with the plasmid pTSMI (FIG. 2). The EcoRI fragment with a methylase gene deleted at the C-terminal end was recloned in M13mp19 phages, in which an oligonucleotide directed in vitro mutagenesis (Amersham No. 1523) was then carried out. In this process an oligonucleotide was used which was directed towards the region around the cytosine residue at position 2134 within the arginine codon (CGA) of the DNA sequence SEQ ID NO:1. A nonsense mutation was introduced into the reading frame of the Sau3AI methylase gene in which the C of this arginine codon was converted into a T, which results in the formation of an opal stop codon (TGA). The mutated gene fragment was again cleaved out of the M13mp19 vector with EcoRI and cloned back again into the EcoRI plasmid fragment of pTSM1.

The stop codon within the mutated methylase gene is read over at a rate of about 10% of the original activity, in particular when it is followed by one or several adenine residues (Parker, Microbiol. Res. 53 (1989), 273–298). A tryptophan is incorporated instead of a stop codon. In this way a mutated Sau3AI methylase is formed.

A derivative of pBT-SM11 containing this mutated methylase gene, which was denoted pBT-SM11/2, can be transformed back and forth between E. coli and S. carnosus without difficulty and in both organisms causes the DNA to be resistant to cleavage by Sau3AI. Thus the incompatibility of the Sau3AI methylase with E. coli is reduced by the mutation to such an extent that a cloning of this gene in E. coli is possible.

The insertion of the 3.68 kb mutated methylase gene (SacI/XbaI fragment) of pBT-SM11/2 could be incorporated into the multiple cloning site of pUC18 (SacI/XbaI) and successfully cloned in different E. coli K12 strains (e.g. JM83). The resulting vector was denoted pUSM1 and is shown in FIG. 6.

EXAMPLE 3

Cloning of the Sau3AI endonuclease in E. coli JM83

3.1 Cloning of the promoter-free Sau3AI endonuclease gene downstream of the repressible fdhF promoter The fdhF promoter:

The fdh gene codes for the selenium peptide of formate dehydrogenase which forms the formate-hydrogen-lyase complex together with the hydrogenase isoenzyme 3 and yet unknown electron carriers.

The fdhF gene expression is induced by anaerobic conditions and formate and is repressed by small amounts of oxygen. The fdhF promoter (with the urs sequence (upstream regulatory sequence) and a small part of the fdhF gene) was subcloned on the plasmid pBN208 (DSM 4069P) (Birkmann et al., Arch. Microbiol 148 (1987), 273–298). The DNA sequences of the fdhF promoter and the fdhF gene are described (see also EP-A 0 285 152).

Starting with the plasmid pBN208, the fdhF promoter sequence up to just before the Shine-Dalgarno (SD) sequence of the fdhF gene was amplified by means of the polymerase chain reaction (PCR; with the Taq polymerase) (Innis et al., PCR Protocols. A Guide to Methods and Applications. Acad. Press. Inc., 1990). Two oligonucleotides were synthesized for this. The first oligonucleotide was directed towards the sequence upstream of the EcoRI cleavage site (cf. FIG. 7, No. 6 and 7). The second oligonucleotide was directed towards the sequence around the SD sequence of the fdhF gene. It was altered in such a way that after amplification by means of PCR a second EcoRI cleavage site was formed a few nucleotides upstream of the SD sequence. The DNA fragment containing the fdhF promoter sequence amplified in this way was recleaved with EcoRI. In this way the DNA fragment was provided with an EcoRI cleavage site on both sides.

Sau3AI gene without promoter on the vector pUCBM21(T)-Sau3AIR (-P):

As can be seen in FIG. 7, No. 1 to 5 and from the plasmid map of pSEM7, a Sau3AIR gene fragment was cleaved out by a double cleavage with SalI/HindIII and ligated into the phage M13mp19 which had also been cleaved with SalI/HindIII. Then an "oligonucleotide directed in vitro mutagenesis" (Amersham No. 1523) was carried out there in a region a few nucleotides upstream of the SD sequence of the Sau3AIR gene fragment in M13mp19-Sau3AIR'. After preparation of single-stranded DNA, the corresponding oligonucleotide was hybridized to the single-stranded DNA for this and an elongation in the 5'-3' direction beyond the oligonucleotide is carried out using Klenow polymerase, ligase and the four nucleotide triphosphates dATP, dCTP, dGTP, dTTP. The DNA which is now double-stranded is transformed in E. coli JM83. Recombinant clones are picked and the single-stranded DNA of the M13 phages contained therein is isolated from them. A DNA sequencing at the mutagenesis site is carried out according to known techniques and thus the exact base exchange for the desired mutation is checked In this case it was found that the sequence 5'-GCGGAAATAATTATTTAATGTTAAGAGGGG-3' (SEQ ID NO:4) (the last 5 bases AGGGG define the SD sequence) had been mutagenized into the sequence 5'-GCGGAAAGAATTCTTTAATGT-TAAGAGGGG-3' (SEQ ID No:5). An EcoRI cleavage site was formed in this way (5'-GAATTC, underlined sequence).

The Sau3AIR' gene fragment without promoter could be cleaved out by an EcoRI/EcoRV double cleavage of the double-stranded form of M13mp19-Sau3AIR' (mut) and incorporated into the vector pUCBM21 (T) cleaved with EcoRI/EcoRV. This vector contains an oligonucleotide with the λT₀ terminator (E. Schwarz et al., Nature 272 (1978), 410–414) in the PvuI site of pUCBM21 (Boehringer Mannheim, Cat. No. 1219251). Other commercial vectors with suitable cloning sites e.g. the pUC vectors can of course also be used instead of pUCBM21.

The plasmid pUC(T)-Sau3AIR'(-P) which formed was cleaved with EcoRV and HindIII. The HindIII site was subsequently blunt-ended by treatment with Klenow polymerase. Apart from this pSEM7 was also cleaved with EcoRV and BstNI, the 745 bp DNA fragment was isolated, the BstNI site was blunt-ended by treatment with Klenow polymerase and the resulting fragment was ligated with the cleaved vector pUC(T)-Sau3AIR'(-P). In this way the coding sequence of the Sau3AIR gene was again made complete. However, the Sau3AIR gene no longer has a promoter on the resulting construct.

In the construction of the Sau3AI endonuclease expression vector care must be taken that the promoterless Sau3AIR gene is not incorporated in the same transcription direction as the lacZ gene in the pUC vector since otherwise a transcription of the Sau3AIR gene of the lacZ promoter would take place which is lethal for the cell. In addition the expression vector contains an effective terminator before the insertion site of the promoterless Sau3AIR gene (in the direction of transcription) in order to prevent a "read through" of previous genes.

The amplified fdhF promoter fragment recleaved with EcoRI was incorporated into the EcoRI cleavage site of the above vector containing the Sau3AIR gene without promoter. The ligation preparation was transformed in E. coli JM83. The high-copy plasmid pUC(T)-Sau3AIR-P(fdhF) which formed contains the Sau3AIR gene under the control of the regulatable fdhF promoter. The promoter is repressed when supplied with oxygen; under oxygen deficiency and addition of formate the promoter is de-repressed and the Sau3AIR gene can be transcribed and the mRNA which forms can be translated. The construction of the vector pUC(T)-Sau3AIR-P(fdhF) is shown diagrammatically in FIG. 7.

3.2 Construction of a compatible vector which contains the mutated Sau3AI methylase gene In order to ensure a complete protection of the DNA of a cell which is transformed with a Sau3AIR expression vector, the Sau3AI methylase gene which is only expressed to a small extent after mutagenesis according to Example 2 but can thereby be cloned in E. coli, was incorporated as a SacI/XbaI fragment into the vector pACYC184 (Chang and Cohen, J. Bacteriol. 134 (1978), 1141–1156) which is compatible with pUC and cloned in E. coli JM83 transformed with pUC-Sau3AIR-P(fdhF). The methylase present in relatively small amounts in the doubly transformed cells now ensures an adequate protection against the Sau3AI endonuclease which is also formed in the repressed state in very small amounts by methylation of the Sau3AI cleavage sites.

---

( 1 ) GENERAL INFORMATION:

( i i i ) NUMBER OF SEQUENCES: 5

( v i ) CURRENT APPLICATION DATA:
        ( A ) APPLICATION NUMBER: US 07/712,833
        ( B ) FILING DATE: 10-JUN-1991

( 2 ) INFORMATION FOR SEQ ID NO:1:

( i ) SEQUENCE CHARACTERISTICS:
        ( A ) LENGTH: 3360 base pairs
        ( B ) TYPE: nucleic acid 5,175,101

-continued (C) STRANDEDNESS: double
(D) TOPOLOGY: linear (ii) MOLECULE TYPE: DNA (genomic)

(ix) FEATURE:
    (A) NAME/KEY: CDS
    (B) LOCATION: 448..1914
    (D) OTHER INFORMATION: /function="Cleaves in front of G residue of palindrome sequence"
    / product="Sau3A1 restriction endonuclease"

(ix) FEATURE:
    (A) NAME/KEY: CDS
    (B) LOCATION: 2017..3252
    (D) OTHER INFORMATION: /function="Modifies C residues to protect DNA from cleavage"
    / product="Sau3AUI methyl transferase"

(xi) SEQUENCE DESCRIPTION: SEQ ID NO:1:

```
AAGTCGACCT TCACCAAGAC CGAATTTTCC GCGTATACCC GCAGTACCAA ACGTTAATTT      60

ACTTTCAAAA CCTTCTCGCT GTTCAATGTC AGATTGCTGC TCATAAAAAT GTTTAACTAA    120

ACTATCATTA GCTCTTTCTA TCCATAATTC TTTATCCATT GTTGCTAAAC ATCCTTTCAA    180

AATCTCAGTT AGACTTAATA AAACATGAAA ACTAAAGCCC TTACATTTAT GTAATGAATT    240

ATAAAGAAAT ACGCCCCAAA AGTAAAAAAA CACAGCCCCA AGACAATACT TTTCACAAGT    300

ATTATATAAT AGATGTGTAT GAAAATGCAT GGAGTAGATG TAAGAGTGAT ATTCAAAATG    360

TGTAAAAAAT ATGGATAATT CTATATAATT ATATTATTGA AATTTTAAAT AGCGGAAATA    420

ATTATTTAAT GTTAAGAGGG GATAATT TTG GAA AGT TAT TTG ACA AAA CAA       471
                                 Leu Glu Ser Tyr Leu Thr Lys Gln
                                  1               5
```

```
GCC GTA CAT AAT CGC GCA AAA GAA GCT GTT GGT AAA AGT GTA TTA GAA     519
Ala Val His Asn Arg Ala Lys Glu Ala Val Gly Lys Ser Val Leu Glu
        10              15                  20

TTA AAT GGT GGT GAA TCG ATT AAA CAA AGT AAG AGT TCA GTT GGT GAT     567
Leu Asn Gly Gly Glu Ser Ile Lys Gln Ser Lys Ser Ser Val Gly Asp
 25              30                  35                      40

GCA TTT GAA AAT TGG TTT GGT AAG AAA AAA GAC AGT GAT AGT AAA CCA     615
Ala Phe Glu Asn Trp Phe Gly Lys Lys Lys Asp Ser Asp Ser Lys Pro
                 45                  50                  55

GAT ATG GCA GAA GCT GGG GTG GAA CTT AAG GCA ACG CCA TTT AAA AAG     663
Asp Met Ala Glu Ala Gly Val Glu Leu Lys Ala Thr Pro Phe Lys Lys
             60                  65                  70

TTG AAA AAC GGA AAG TAT AGC TCC AAA GAA AGA TTA GTA TTA AAT ATT     711
Leu Lys Asn Gly Lys Tyr Ser Ser Lys Glu Arg Leu Val Leu Asn Ile
         75                  80                  85

ATA AAC TAT GAG AAA GTG GCA AAT GAA AAT TTT GAA ACT AGT AGT TTT     759
Ile Asn Tyr Glu Lys Val Ala Asn Glu Asn Phe Glu Thr Ser Ser Phe
     90                  95                 100

TTA TCT AAG AAT AAT ACT ATA GAA TTA GCT TTC TAT GAA TAT ATC AAG     807
Leu Ser Lys Asn Asn Thr Ile Glu Leu Ala Phe Tyr Glu Tyr Ile Lys
105                 110                 115                 120

GGA ACA CCT AGT GAT AAT TGG ATT ATT AAA GAA GCG GTG CTT TAT GAA     855
Gly Thr Pro Ser Asp Asn Trp Ile Ile Lys Glu Ala Val Leu Tyr Glu
                125                 130                 135

ATG CAT AAA AAC CCG ATT GAT TAT GAA ATA ATT AAA CAA GAT TGG GAA     903
Met His Lys Asn Pro Ile Asp Tyr Glu Ile Ile Lys Gln Asp Trp Glu
            140                 145                 150

ATA ATA AAT CAA TAT ATT AAT GAA GGA AAG GCA CAT GAA TTG AGT GAA     951
Ile Ile Asn Gln Tyr Ile Asn Glu Gly Lys Ala His Glu Leu Ser Glu
        155                 160                 165

GGT TTG ACA AGT TAT TTA GCG CCA TGT ACA AAG GGT GCG AAT GCT AGT     999
```

|     |     |     |     |     |     |     |     |     |     |     |     |     |     |     |     |     |
|---|---|---|---|---|---|---|---|---|---|---|---|---|---|---|---|---|
| Gly | Leu | Thr | Ser | Tyr | Leu | Ala | Pro | Cys | Thr | Lys | Gly | Ala | Asn | Ala | Ser | |
| | 170 | | | | 175 | | | | | 180 | | | | | | |

| TCT | TTA | AGA | AAT | CAG | CCT | TAT | TCA | GAC | ATA | AAA | GCA | AAG | CAA | AGA | GCA | 1047 |
|---|---|---|---|---|---|---|---|---|---|---|---|---|---|---|---|---|
| Ser | Leu | Arg | Asn | Gln | Pro | Tyr | Ser | Asp | Ile | Lys | Ala | Lys | Gln | Arg | Ala | |
| 185 | | | | | 190 | | | | | 195 | | | | | 200 | |

| TTT | TCT | TTG | AAG | TCT | GGG | TAT | ATG | ACA | TCT | ATT | TTA | CGC | AAA | TAT | GTT | 1095 |
|---|---|---|---|---|---|---|---|---|---|---|---|---|---|---|---|---|
| Phe | Ser | Leu | Lys | Ser | Gly | Tyr | Met | Thr | Ser | Ile | Leu | Arg | Lys | Tyr | Val | |
| | | | | 205 | | | | | 210 | | | | | 215 | | |

| CTA | GGT | GAT | GAA | AAA | ATA | GAT | TCA | ATT | GTC | AAA | GAC | CCA | TTT | GAA | ATA | 1143 |
|---|---|---|---|---|---|---|---|---|---|---|---|---|---|---|---|---|
| Leu | Gly | Asp | Glu | Lys | Ile | Asp | Ser | Ile | Val | Lys | Asp | Pro | Phe | Glu | Ile | |
| | | | | 220 | | | | | 225 | | | | | 230 | | |

| AAA | GAA | AAA | TCA | ATA | GAG | GAC | ATA | GTC | TTT | GAA | AAA | TTT | CAG | CCA | TAT | 1191 |
|---|---|---|---|---|---|---|---|---|---|---|---|---|---|---|---|---|
| Lys | Glu | Lys | Ser | Ile | Glu | Asp | Ile | Val | Phe | Glu | Lys | Phe | Gln | Pro | Tyr | |
| | | | 235 | | | | | 240 | | | | | 245 | | | |

| ATA | AAC | TGG | TCA | ATC | GAT | AAA | TTA | TGC | GAA | CAT | TTT | TCT | ATC | AAT | AAA | 1239 |
|---|---|---|---|---|---|---|---|---|---|---|---|---|---|---|---|---|
| Ile | Asn | Trp | Ser | Ile | Asp | Lys | Leu | Cys | Glu | His | Phe | Ser | Ile | Asn | Lys | |
| 250 | | | | | 255 | | | | | 260 | | | | | | |

| GGT | GAG | AAA | GGT | TTA | AAT | TAT | AGA | ATA | GCC | TCT | GCC | ATT | TTA | AAT | CTA | 1287 |
|---|---|---|---|---|---|---|---|---|---|---|---|---|---|---|---|---|
| Gly | Glu | Lys | Gly | Leu | Asn | Tyr | Arg | Ile | Ala | Ser | Ala | Ile | Leu | Asn | Leu | |
| 265 | | | | | 270 | | | | | 275 | | | | | 280 | |

| AAA | GGT | AAA | ACT | ACT | AAA | AGT | AAA | CCA | TTC | CCG | GAA | GTT | GAA | GAG | TTT | 1335 |
|---|---|---|---|---|---|---|---|---|---|---|---|---|---|---|---|---|
| Lys | Gly | Lys | Thr | Thr | Lys | Ser | Lys | Pro | Phe | Pro | Glu | Val | Glu | Glu | Phe | |
| | | | | 285 | | | | | 290 | | | | | 295 | | |

| GAA | AAA | TCA | TCT | ATA | GTA | GTC | AAA | ACA | GTT | CAT | TTT | AAT | AAA | AAG | AAT | 1383 |
|---|---|---|---|---|---|---|---|---|---|---|---|---|---|---|---|---|
| Glu | Lys | Ser | Ser | Ile | Val | Val | Lys | Thr | Val | His | Phe | Asn | Lys | Lys | Asn | |
| | | | 300 | | | | | 305 | | | | | 310 | | | |

| GTG | AAT | AAA | GAA | AGT | ATG | TCA | TTT | GGA | GCT | TTT | AAA | TTT | GAA | GAA | CTA | 1431 |
|---|---|---|---|---|---|---|---|---|---|---|---|---|---|---|---|---|
| Val | Asn | Lys | Glu | Ser | Met | Ser | Phe | Gly | Ala | Phe | Lys | Phe | Glu | Glu | Leu | |
| | | 315 | | | | | 320 | | | | | 325 | | | | |

| GCT | AAT | GAG | GAA | TGG | GAA | GAT | AGT | GAA | GGA | TAT | CCT | AGT | GCA | CAA | TGG | 1479 |
|---|---|---|---|---|---|---|---|---|---|---|---|---|---|---|---|---|
| Ala | Asn | Glu | Glu | Trp | Glu | Asp | Ser | Glu | Gly | Tyr | Pro | Ser | Ala | Gln | Trp | |
| 330 | | | | | 335 | | | | | 340 | | | | | | |

| CGA | AAC | TTT | TTG | TTA | GAA | ACA | AGG | TTT | TTA | TTT | TTT | GTT | GTT | AAA | GAA | 1527 |
|---|---|---|---|---|---|---|---|---|---|---|---|---|---|---|---|---|
| Arg | Asn | Phe | Leu | Leu | Glu | Thr | Arg | Phe | Leu | Phe | Phe | Val | Val | Lys | Glu | |
| 345 | | | | | 350 | | | | | 355 | | | | | 360 | |

| GAT | GAA | GAT | GGT | GTA | GAC | ATA | TTC | AAA | GGA | ATA | AAA | TTT | TTT | AGT | ATG | 1575 |
|---|---|---|---|---|---|---|---|---|---|---|---|---|---|---|---|---|
| Asp | Glu | Asp | Gly | Val | Asp | Ile | Phe | Lys | Gly | Ile | Lys | Phe | Phe | Ser | Met | |
| | | | | 365 | | | | | 370 | | | | | 375 | | |

| CCT | GAA | GAA | GAC | ATA | AAC | GGA | CCT | GTC | AAA | AGA | ATG | TGG | GAT | GAT | ACA | 1623 |
|---|---|---|---|---|---|---|---|---|---|---|---|---|---|---|---|---|
| Pro | Glu | Glu | Asp | Ile | Asn | Gly | Pro | Val | Lys | Arg | Met | Trp | Asp | Asp | Thr | |
| | | | 380 | | | | | 385 | | | | | 390 | | | |

| GTG | AAG | AAA | TTA | AAA | GAG | GGT | GTC | ACA | TTA | GAA | GCT | GTA | CCG | GAC | AAA | 1671 |
|---|---|---|---|---|---|---|---|---|---|---|---|---|---|---|---|---|
| Val | Lys | Lys | Leu | Lys | Glu | Gly | Val | Thr | Leu | Glu | Ala | Val | Pro | Asp | Lys | |
| | | 395 | | | | | 400 | | | | | 405 | | | | |

| AGT | ACA | AAG | GAT | GGT | TGG | AGA | ATA | AAA | AAT | AAT | TTT | GTA | GAT | AAA | AGT | 1719 |
|---|---|---|---|---|---|---|---|---|---|---|---|---|---|---|---|---|
| Ser | Thr | Lys | Asp | Gly | Trp | Arg | Ile | Lys | Asn | Asn | Phe | Val | Asp | Lys | Ser | |
| 410 | | | | | 415 | | | | | 420 | | | | | | |

| GAT | GAT | TTA | ATT | TGC | CAT | GTT | AGA | CCA | CAC | ACT | AAT | AAC | AGA | GAC | TAT | 1767 |
|---|---|---|---|---|---|---|---|---|---|---|---|---|---|---|---|---|
| Asp | Asp | Leu | Ile | Cys | His | Val | Arg | Pro | His | Thr | Asn | Asn | Arg | Asp | Tyr | |
| 425 | | | | | 430 | | | | | 435 | | | | | 440 | |

| CGT | GGA | GGA | AGT | AAT | GCA | GAT | AAG | CTT | CCT | AAA | AAG | ATT | AAC | TGG | ATT | 1815 |
|---|---|---|---|---|---|---|---|---|---|---|---|---|---|---|---|---|
| Arg | Gly | Gly | Ser | Asn | Ala | Asp | Lys | Leu | Pro | Lys | Lys | Ile | Asn | Trp | Ile | |
| | | | | 445 | | | | | 450 | | | | | 455 | | |

| AAT | AGA | CCT | GAC | TCA | GAT | GAT | TAT | TCG | GAT | GAG | TGG | ATG | ACT | AAA | CAA | 1863 |
|---|---|---|---|---|---|---|---|---|---|---|---|---|---|---|---|---|
| Asn | Arg | Pro | Asp | Ser | Asp | Asp | Tyr | Ser | Asp | Glu | Trp | Met | Thr | Lys | Gln | |
| | | | 460 | | | | | 465 | | | | | 470 | | | |

| AGT | TTT | TGG | ATA | AAT | AAT | GAC | TAC | ATA | AAA | AAG | CAA | GTT | GAA | GAT | TTA | 1911 |
|---|---|---|---|---|---|---|---|---|---|---|---|---|---|---|---|---|
| Ser | Phe | Trp | Ile | Asn | Asn | Asp | Tyr | Ile | Lys | Lys | Gln | Val | Glu | Asp | Leu | |
| | | 475 | | | | | 480 | | | | | 485 | | | | |

| TTG | TAGTTAAAGT | ATGTTAAAAT | ATAAGATATT | CTTTAAAAT | ATCGAACGAT | 1964 |
|---|---|---|---|---|---|---|
| Leu | | | | | | |

```
CGTTCGTATT TTGTGTTATA ATAAGGTTGA ATTAAGTATA GGAGGTCGCC TA ATG              2019
                                                          Met
                                                          1

AAT AAA ATT AAA GTA GTA GAA TTG TTT GCG GGT GTA GGC GGG TTT CGT           2067
Asn Lys Ile Lys Val Val Glu Leu Phe Ala Gly Val Gly Gly Phe Arg
            5               10                  15

TTA GGT TTA GAA AAT ACG AAA AAT GGT ATA TTT GAC ATA ACT TGG GCA           2115
Leu Gly Leu Glu Asn Thr Lys Asn Gly Ile Phe Asp Ile Thr Trp Ala
        20              25                  30

AAT CAA TGG GAG CCC TCA CGA AAA ATC CAA CAT GCA TTT GAT TGT TAT           2163
Asn Gln Trp Glu Pro Ser Arg Lys Ile Gln His Ala Phe Asp Cys Tyr
        35              40                  45

AGT AAA AGA TTT AAG AAC GGC ATC CAT AGT AAT AAG GAT ATT GCC CAG           2211
Ser Lys Arg Phe Lys Asn Gly Ile His Ser Asn Lys Asp Ile Ala Gln
50              55                  60                          65

GTA TCT GAT GAA GAA ATG GCA AAT ACT GAA GCT GAT ATG ATT GTA GGA           2259
Val Ser Asp Glu Glu Met Ala Asn Thr Glu Ala Asp Met Ile Val Gly
                70                  75                  80

GGA TTT CCT TGC CAA GAT TAT TCA GTT GCA AGG AGT TTA AAT GGA GAA           2307
Gly Phe Pro Cys Gln Asp Tyr Ser Val Ala Arg Ser Leu Asn Gly Glu
            85                  90                  95

TTA GGA ATA CAA GGA AAA AAG GGC GTT TTA TTC TGG CAA ATT ATT AGA           2355
Leu Gly Ile Gln Gly Lys Lys Gly Val Leu Phe Trp Gln Ile Ile Arg
        100                 105                 110

TAT ATT CAA AAT ACA TTT CCT AAA TAC TTG TTG CTT GAA AAT GTT GAT           2403
Tyr Ile Gln Asn Thr Phe Pro Lys Tyr Leu Leu Leu Glu Asn Val Asp
115                 120                 125

AGA TTA TTG AAA TCA CCT TCG AGT CAG AGA GGG AGA GAC TTT GCT GTA           2451
Arg Leu Leu Lys Ser Pro Ser Ser Gln Arg Gly Arg Asp Phe Ala Val
130                 135                 140                         145

ATG TTA TCA ACC TTA AAT GAG TTA GGC TAT AAT GTT GAA TGG CGC GTG           2499
Met Leu Ser Thr Leu Asn Glu Leu Gly Tyr Asn Val Glu Trp Arg Val
                150                 155                 160

ATT AAT GCT GCT GAT TAT GGC AAT GCT CAA AGA CGT AGA AGG GTA TTT           2547
Ile Asn Ala Ala Asp Tyr Gly Asn Ala Gln Arg Arg Arg Arg Val Phe
            165                 170                 175

ATA TTT GGA TAT AAG CAA GAT TTA AAC TAT AGC AAA GCT ATG GAA GAA           2595
Ile Phe Gly Tyr Lys Gln Asp Leu Asn Tyr Ser Lys Ala Met Glu Glu
        180                 185                 190

AGT CCG TTG GAT AAA ATT ATA TAT CAC AAT GGT TTG TTT GCT GAA GCT           2643
Ser Pro Leu Asp Lys Ile Ile Tyr His Asn Gly Leu Phe Ala Glu Ala
195                 200                 205

TTT CCG ATT GAA GAT TAT GCC AAT AAA AAT AGA GTA AAT AGG ACT CAT           2691
Phe Pro Ile Glu Asp Tyr Ala Asn Lys Asn Arg Val Asn Arg Thr His
210                 215                 220                         225

ATT ACT CAT GAT ATA GTC GAT ATT TCA GAT AAT TTC AGT TTT CAA TTT           2739
Ile Thr His Asp Ile Val Asp Ile Ser Asp Asn Phe Ser Phe Gln Phe
                230                 235                 240

TAT AAT AGT GGA ATC ATG AAA AAT GGA GAA ATT TTA ACT ATT GAC ACA           2787
Tyr Asn Ser Gly Ile Met Lys Asn Gly Glu Ile Leu Thr Ile Asp Thr
            245                 250                 255

ATA CCA AAA TAT GAA AAA TCA GTA ACC TTA GGA GAA ATT ATT GAA AGT           2835
Ile Pro Lys Tyr Glu Lys Ser Val Thr Leu Gly Glu Ile Ile Glu Ser
        260                 265                 270

AAT GTA GAT GAT GGT TTT TCA TTA AAT CAA GAT CAA ATT GAT AAA TTT           2883
Asn Val Asp Asp Gly Phe Ser Leu Asn Gln Asp Gln Ile Asp Lys Phe
275                 280                 285

AAA TAT TTA AGA GGA CCC AAA AAG ATT AAA CGA ACT ACT AAA GAT GGT           2931
Lys Tyr Leu Arg Gly Pro Lys Lys Ile Lys Arg Thr Thr Lys Asp Gly
290                 295                 300                         305

CAT GAA TAT TAT TTT TCA GAA GGT GGT ATG TCT GAA ACA GAT TCA TTA           2979
```

|         |         |         |         |         |         |         |         |         |         |         |         |         |         |      |
|---------|---------|---------|---------|---------|---------|---------|---------|---------|---------|---------|---------|---------|---------|------|
| His | Glu | Tyr | Tyr | Phe | Ser | Glu | Gly | Gly | Met | Ser | Glu | Thr | Asp | Ser | Leu |
|     |     |     |     | 310 |     |     |     |     | 315 |     |     |     |     |     | 320 |

```
GAG TTA CCT GCA AGA ACA ATG CTT ACA AGT GAA TCA TCT ATT AAT AGA       3027
Glu Leu Pro Ala Arg Thr Met Leu Thr Ser Glu Ser Ser Ile Asn Arg
            325                 330                 335

AGT ACT CAT TTT TTA AAC GTA GAT GGT GTT TAT AGA ACT TTG ACA CCT       3075
Ser Thr His Phe Leu Asn Val Asp Gly Val Tyr Arg Thr Leu Thr Pro
            340                 345                 350

ATT GAA GCA GAA AGG TTG AAT GGG TTT CCA GAT AAT TGG ACA GAA GGT       3123
Ile Glu Ala Glu Arg Leu Asn Gly Phe Pro Asp Asn Trp Thr Glu Gly
            355                 360                 365

ATG CCA ATT AAG ATG AGA TAC TTT TGT ATG GGC AAT GCT CTT GTT GTG       3171
Met Pro Ile Lys Met Arg Tyr Phe Cys Met Gly Asn Ala Leu Val Val
370             375                 380                 385

CCT TTG ATT ACT AGA ATA GGT AAT CAA ATT GAA AAA ATT GAT AGT ATT       3219
Pro Leu Ile Thr Arg Ile Gly Asn Gln Ile Glu Lys Ile Asp Ser Ile
            390                 395                 400

ACA AAT GAT GAA TTC AGT CAG CTA CGT TTA TTT TAAATAAATC AAATGTAGAG     3272
Thr Asn Asp Glu Phe Ser Gln Leu Arg Leu Phe
            405                 410

TGCGTTTGAT TTAACAAGTT TGTATACTAA AGATTCATAG ATTATTGTAT ATTGACCAGT     3332

ATTTATCAGC GTATTATTTT AATATATA                                        3360
```

( 2 ) INFORMATION FOR SEQ ID NO:2:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu Glu Ser Tyr Leu Thr Lys Gln Ala Val His Asn Arg Ala Lys Glu
 1               5                  10                  15

Ala Val Gly Lys Ser Val Leu Glu Leu Asn Gly Gly Glu Ser Ile Lys
            20                  25                  30

Gln Ser Lys Ser Ser Val Gly Asp Ala Phe Glu Asn Trp Phe Gly Lys
            35                  40                  45

Lys Lys Asp Ser Asp Ser Lys Pro Asp Met Ala Glu Ala Gly Val Glu
 50                  55                  60

Leu Lys Ala Thr Pro Phe Lys Lys Leu Lys Asn Gly Lys Tyr Ser Ser
 65                  70                  75                  80

Lys Glu Arg Leu Val Leu Asn Ile Ile Asn Tyr Glu Lys Val Ala Asn
            85                  90                  95

Glu Asn Phe Glu Thr Ser Ser Phe Leu Ser Lys Asn Asn Thr Ile Glu
            100                 105                 110

Leu Ala Phe Tyr Glu Tyr Ile Lys Gly Thr Pro Ser Asp Asn Trp Ile
            115                 120                 125

Ile Lys Glu Ala Val Leu Tyr Glu Met His Lys Asn Pro Ile Asp Tyr
            130                 135                 140

Glu Ile Ile Lys Gln Asp Trp Glu Ile Ile Asn Gln Tyr Ile Asn Glu
145                 150                 155                 160

Gly Lys Ala His Glu Leu Ser Glu Gly Leu Thr Ser Tyr Leu Ala Pro
            165                 170                 175

Cys Thr Lys Gly Ala Asn Ala Ser Ser Leu Arg Asn Gln Pro Tyr Ser
            180                 185                 190

Asp Ile Lys Ala Lys Gln Arg Ala Phe Ser Leu Lys Ser Gly Tyr Met
            195                 200                 205
```

```
Thr Ser Ile Leu Arg Lys Tyr Val Leu Gly Asp Glu Lys Ile Asp Ser
    210             215             220

Ile Val Lys Asp Pro Phe Glu Ile Lys Glu Lys Ser Ile Glu Asp Ile
225             230             235                         240

Val Phe Glu Lys Phe Gln Pro Tyr Ile Asn Trp Ser Ile Asp Lys Leu
            245             250             255

Cys Glu His Phe Ser Ile Asn Lys Gly Glu Lys Gly Leu Asn Tyr Arg
            260             265             270

Ile Ala Ser Ala Ile Leu Asn Leu Lys Gly Lys Thr Thr Lys Ser Lys
        275             280             285

Pro Phe Pro Glu Val Glu Glu Phe Glu Lys Ser Ser Ile Val Val Lys
    290             295             300

Thr Val His Phe Asn Lys Lys Asn Val Asn Lys Glu Ser Met Ser Phe
305             310             315             320

Gly Ala Phe Lys Phe Glu Glu Leu Ala Asn Glu Glu Trp Glu Asp Ser
            325             330             335

Glu Gly Tyr Pro Ser Ala Gln Trp Arg Asn Phe Leu Leu Glu Thr Arg
            340             345             350

Phe Leu Phe Phe Val Val Lys Glu Asp Glu Asp Gly Val Asp Ile Phe
            355             360             365

Lys Gly Ile Lys Phe Phe Ser Met Pro Glu Glu Asp Ile Asn Gly Pro
    370             375             380

Val Lys Arg Met Trp Asp Asp Thr Val Lys Lys Leu Lys Glu Gly Val
385             390             395             400

Thr Leu Glu Ala Val Pro Asp Lys Ser Thr Lys Asp Gly Trp Arg Ile
            405             410             415

Lys Asn Asn Phe Val Asp Lys Ser Asp Asp Leu Ile Cys His Val Arg
            420             425             430

Pro His Thr Asn Asn Arg Asp Tyr Arg Gly Gly Ser Asn Ala Asp Lys
        435             440             445

Leu Pro Lys Lys Ile Asn Trp Ile Asn Arg Pro Asp Ser Asp Asp Tyr
    450             455             460

Ser Asp Glu Trp Met Thr Lys Gln Ser Phe Trp Ile Asn Asn Asp Tyr
465             470             475             480

Ile Lys Lys Gln Val Glu Asp Leu Leu
                485
```

( 2 ) INFORMATION FOR SEQ ID NO:3:

( i ) SEQUENCE CHARACTERISTICS:
        ( A ) LENGTH: 412 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Asn Lys Ile Lys Val Val Glu Leu Phe Ala Gly Val Gly Gly Phe
1               5               10              15

Arg Leu Gly Leu Glu Asn Thr Lys Asn Gly Ile Phe Asp Ile Thr Trp
            20              25              30

Ala Asn Gln Trp Glu Pro Ser Arg Lys Ile Gln His Ala Phe Asp Cys
        35              40              45

Tyr Ser Lys Arg Phe Lys Asn Gly Ile His Ser Asn Lys Asp Ile Ala
    50              55              60

Gln Val Ser Asp Glu Glu Met Ala Asn Thr Glu Ala Asp Met Ile Val
65              70              75              80

Gly Gly Phe Pro Cys Gln Asp Tyr Ser Val Ala Arg Ser Leu Asn Gly
```

|  |  |  |  |  | 85 |  |  |  |  | 90 |  |  |  |  | 95 |  |  |
|---|---|---|---|---|---|---|---|---|---|---|---|---|---|---|---|---|---|
| Glu | Leu | Gly | Ile | Gln | Gly | Lys | Lys | Gly | Val | Leu | Phe | Trp | Gln | Ile | Ile |
|  |  |  | 100 |  |  |  |  | 105 |  |  |  | 110 |  |  |  |
| Arg | Tyr | Ile | Gln | Asn | Thr | Phe | Pro | Lys | Tyr | Leu | Leu | Leu | Glu | Asn | Val |
|  |  | 115 |  |  |  |  | 120 |  |  |  |  | 125 |  |  |  |
| Asp | Arg | Leu | Leu | Lys | Ser | Pro | Ser | Ser | Gln | Arg | Gly | Arg | Asp | Phe | Ala |
|  | 130 |  |  |  |  | 135 |  |  |  |  | 140 |  |  |  |  |
| Val | Met | Leu | Ser | Thr | Leu | Asn | Glu | Leu | Gly | Tyr | Asn | Val | Glu | Trp | Arg |
| 145 |  |  |  |  | 150 |  |  |  |  | 155 |  |  |  |  | 160 |
| Val | Ile | Asn | Ala | Ala | Asp | Tyr | Gly | Asn | Ala | Gln | Arg | Arg | Arg | Arg | Val |
|  |  |  |  | 165 |  |  |  |  | 170 |  |  |  |  | 175 |  |
| Phe | Ile | Phe | Gly | Tyr | Lys | Gln | Asp | Leu | Asn | Tyr | Ser | Lys | Ala | Met | Glu |
|  |  |  | 180 |  |  |  |  | 185 |  |  |  |  | 190 |  |  |
| Glu | Ser | Pro | Leu | Asp | Lys | Ile | Ile | Tyr | His | Asn | Gly | Leu | Phe | Ala | Glu |
|  |  | 195 |  |  |  |  |  | 200 |  |  |  |  | 205 |  |  |
| Ala | Phe | Pro | Ile | Glu | Asp | Tyr | Ala | Asn | Lys | Asn | Arg | Val | Asn | Arg | Thr |
|  |  | 210 |  |  |  |  | 215 |  |  |  |  | 220 |  |  |  |
| His | Ile | Thr | His | Asp | Ile | Val | Asp | Ile | Ser | Asp | Asn | Phe | Ser | Phe | Gln |
| 225 |  |  |  |  | 230 |  |  |  |  | 235 |  |  |  |  | 240 |
| Phe | Tyr | Asn | Ser | Gly | Ile | Met | Lys | Asn | Gly | Glu | Ile | Leu | Thr | Ile | Asp |
|  |  |  |  | 245 |  |  |  |  | 250 |  |  |  |  | 255 |  |
| Thr | Ile | Pro | Lys | Tyr | Glu | Lys | Ser | Val | Thr | Leu | Gly | Glu | Ile | Ile | Glu |
|  |  |  | 260 |  |  |  |  | 265 |  |  |  |  | 270 |  |  |
| Ser | Asn | Val | Asp | Asp | Gly | Phe | Ser | Leu | Asn | Gln | Asp | Gln | Ile | Asp | Lys |
|  |  | 275 |  |  |  |  | 280 |  |  |  |  | 285 |  |  |  |
| Phe | Lys | Tyr | Leu | Arg | Gly | Pro | Lys | Ile | Lys | Arg | Thr | Thr | Lys | Asp |
|  | 290 |  |  |  |  | 295 |  |  |  |  | 300 |  |  |  |  |
| Gly | His | Glu | Tyr | Tyr | Phe | Ser | Glu | Gly | Gly | Met | Ser | Glu | Thr | Asp | Ser |
| 305 |  |  |  |  | 310 |  |  |  |  | 315 |  |  |  |  | 320 |
| Leu | Glu | Leu | Pro | Ala | Arg | Thr | Met | Leu | Thr | Ser | Glu | Ser | Ser | Ile | Asn |
|  |  |  |  | 325 |  |  |  |  | 330 |  |  |  |  | 335 |  |
| Arg | Ser | Thr | His | Phe | Leu | Asn | Val | Asp | Gly | Val | Tyr | Arg | Thr | Leu | Thr |
|  |  |  | 340 |  |  |  |  | 345 |  |  |  |  | 350 |  |  |
| Pro | Ile | Glu | Ala | Glu | Arg | Leu | Asn | Gly | Phe | Pro | Asp | Asn | Trp | Thr | Glu |
|  |  | 355 |  |  |  |  | 360 |  |  |  |  | 365 |  |  |  |
| Gly | Met | Pro | Ile | Lys | Met | Arg | Tyr | Phe | Cys | Met | Gly | Asn | Ala | Leu | Val |
|  | 370 |  |  |  |  | 375 |  |  |  |  | 380 |  |  |  |  |
| Val | Pro | Leu | Ile | Thr | Arg | Ile | Gly | Asn | Gln | Ile | Glu | Lys | Ile | Asp | Ser |
| 385 |  |  |  |  | 390 |  |  |  |  | 395 |  |  |  |  | 400 |
| Ile | Thr | Asn | Asp | Glu | Phe | Ser | Gln | Leu | Arg | Leu | Phe |  |  |  |  |
|  |  |  |  | 405 |  |  |  |  | 410 |  |  |  |  |  |  |

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCGGAAATAA TTATTTAATG TTAAGAGGGG    30

( 2 ) INFORMATION FOR SEQ ID NO:5:

( i ) SEQUENCE CHARACTERISTICS:
        ( A ) LENGTH: 30 base pairs

-continued (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

GCGGAAAGAA TTCTTTAATG TTAAGAGGGG     30

We claim:
1. DNA, comprising:
   (1) at least one of the two regions of the nucleotide sequence SEQ ID NO:1 or a mutation of said nucleotide sequence coding for a protein with a Sau-3AI methylase activity or for a protein with a Sau-3AI endonuclease activity, or
   (2) a sequence complementary to the DNA sequence from (1).
2. DNA comprising at least one of the two regions of the nucleotide sequence SEQ ID NO:1, or a mutation of said nucleotide sequence, coding for a protein with a Sau3AI methylase activity or for a protein with a Sau-3AI endonuclease activity.
3. DNA as claimed in claim 2, wherein one or several mutations which cause a reduction in the total methylase activity when expressed in a cell are introduced within the region coding for a protein with a Sau3AI methylase activity, outside said region or both within and outside said region.
4. DNA as claimed in claim 3, wherein a stop codon followed by at least one A residue is introduced within the region coding for a protein with a Sau3AI methylase activity within the first 1000 bases.
5. DNA as claimed in claim 4, wherein the CGA codon at position 2134-2136 of the nucleotide sequence SEQ ID NO:1 is replaced by a TGA codon.
6. Recombinant vector, wherein it contains one or several copies of a DNA as claimed in claim 2.
7. Recombinant vector as claimed in claim 6, wherein it is suitable for multiplication in prokaryotic organisms.
8. Recombinant vector as claimed in claims 6 or 7, wherein it is a plasmid.
9. Recombinant vector as claimed in claim 6, wherein it contains an origin of replication which is active in *E. coli*.
10. Recombinant vector as claimed in claim 6, wherein it contains a Sau3AI endonuclease gene, a Sau3AI methylase gene or both a Sau3AI endonuclease gene and a Sau3AI methylase gene under the control of a regulatable closed promoter.
11. Recombinant vector as claimed in claim 10, wherein the regulatable closed promoter is a fdhF promoter, a pdoc promoter or a T7 promoter.
12. Recombinant vector as claimed in claim 6, wherein it contains a transcription terminator 5'-upstream of a DNA as claimed in one of the claims 2-5.
13. Microorganism, wherein it is transformed with a DNA as claimed in claim 2 or with a recombinant vector as claimed in claim 5.
14. Microorganism as claimed in claim 13, wherein it did not originally contain a Sau3AI restriction modification system.
15. Microorganism as claimed in claim 13, wherein it already contains the Sau3AI restriction modification system before the transformation.
16. Microorganism as claimed in claim 14, wherein it is transformed with a recombinant vector which contains a Sau3AI endonuclease gene, a Sau3AI methylase gene or both a Sau3AI endonuclease gene and a Sau3AI methylase gene under the control of a regulatable closed promoter.
17. Microorganism as claimed in claim 13, wherein it is transformed with a recombinant vector which contains a Sau3AI endonuclease gene which is under the control of a regulatable closed promoter, and a Sau3AI methylase gene which is tolerated by the microorganism.
18. Microorganism as claimed in claim 13, wherein it is transformed with two vectors which are mutually compatible of which one contains a Sau3AI methylase gene which is tolerated by the microorganism and the other contains a Sau3AI endonuclease gene which is under the control of a regulatable closed promoter.
19. Microorganism as claimed in claim 13, wherein it is a gram-negative bacterium.
20. Microorganism as claimed in claim 19, wherein it is an *E. coli* bacterium.
21. *Staphylococcus carnosus* transformed with the plasmid pSEM7 (DSM 5875).
22. Process for isolating a DNA as claimed in claim 2, wherein
   (1) a gene bank of chromosomal DNA fragments of an original organism which has the Sau3AI restriction modification system is produced by transformation of an organism which is closely related to the original organism and which does not originally have a Sau3AI restriction modification system,
   (2) clones of the transformed organism are tested for Sau3AI methylase activity and
   (3) positive clones with Sau3AI methylase activity are isolated which in addition can contain a gene which codes for a protein with a Sau3AI endonuclease activity.
23. Process as claimed in claim 22, wherein *Staphylococcus aureus* 3AI is used as the original organism.
24. Process as claimed in claims 22 or 23, wherein *Staphylococcus carnosus*, DSM 5875 (without plasmid pSEM7) is used as the closely related organism.
25. Process for the production of a recombinant protein with Sau3AI endonuclease activity, wherein a microorganism as claimed in claim 13, which contains one or several copies of a Sau3AI endonuclease gene, is cultured in a suitable medium under suitable expression conditions and the protein is isolated from the cell extract or the medium.
26. Process as claimed in claim 25, wherein the microorganism contains the Sau3AI endonuclease gene under the control of a regulatable closed promoter.
27. Process as claimed in one of the claims 25 or 26, wherein the microorganism in addition contains a Sau3AI methylase gene which is compatible with it.

* * * * *